United States Patent [19]

Peterson et al.

[11] Patent Number: 5,679,525
[45] Date of Patent: Oct. 21, 1997

[54] EPSTEIN-BARR VIRUS TRANSCRIPTION FACTOR BINDING ASSAY

[75] Inventors: Michael Gregory Peterson, Millbrae; Thomas Henkel, San Francisco, both of Calif.

[73] Assignee: Tularik Inc., South San Francisco, Calif.

[21] Appl. No.: 704,398

[22] Filed: Jul. 17, 1996

Related U.S. Application Data

[63] Continuation of Ser. No. 246,977, May 20, 1994, abandoned.
[51] Int. Cl.⁶ .............................. C12Q 1/68; C12N 15/12
[52] U.S. Cl. .................................................. 435/6; 536/23.5
[58] Field of Search ................................ 435/6; 536/23.5

[56] References Cited

U.S. PATENT DOCUMENTS 4,789,628  12/1988  Nayak ................................... 435/7.94
4,816,730   3/1989  Wilhelm, Jr. et al. ............. 318/568.22

OTHER PUBLICATIONS

Amakawa et al., "Human JkRecombination Signal Binding Protein Gene (IGKJRB): Comparison with its Mouse Homologue", *Genomics* 17:pp. 306-305 (1993).
Ling et al., "EBNA-2 of Herpesvirus Papio Diverges Significantly from the Type A and Type B EBNA-2 Proteins of Epstein-Barr Virus but Retains as Efficient Transactivation Domain with a Conserved Hydrophobic Motif", *J. of Virology* 67(6):pp. 2990-3003 (1993).
Ling et al., "The Epstein-Barr Virus Immortalizing Protein EBNA-2 is Targeted to DNA by a Cellular Enhancer-Binding Protein", *Proc. Natl. Acad. Sci. USA* 90:pp. 9237-9241 (1993).
Matsunami et al., "A Protein Binding to the $J_k$ Recombination Sequence of Immunoglobulin Genes Contains a Sequence Related to the Integrase Motif", *Nature* 342:pp. 934-937 (1989).
Haigh et al., Nature, Mar., 1990, vol. 344:pp. 257-259.
Peterson et al, Trends in Biotechnology, Jan. 1993, vol. 11:pp. 11-18.
Jost et al, Nucleic Acids Research, 1991, vol. 19(10):p. 2788.

Primary Examiner—George C. Elliott
Assistant Examiner—Terry A. McKelvey
Attorney, Agent, or Firm—Richard Aron Osman

[57] ABSTRACT

The invention provides methods and compositions for identifying pharmacological agents useful in the diagnosis or treatment of disease associated with the expression of a gene modulated by a transcription complex containing at least CBF1 and a transcription factor. The methods involve combining CBF1, the Epstein-Barr virus transcription factor EBNA2 or cellular homolog thereof, and a candidate pharmacological agent. This mixture is incubated under conditions whereby, but for the presence of the candidate pharmacological agent, CBF1 binds EBNA2. The absence of selective binding indicates that the candidate pharmacological agent is capable of selectively modulating the expression of a gene dependent on CBF1-transcription factor binding. The mixture may further comprise a CBF1 binding element including the nucleotide sequence: C-G-T-G-G-G-A-A. This mixture is incubated under conditions whereby, but for the presence of the candidate pharmacological agent, a transcription complex comprising both polypeptides bound, directly or indirectly to the nucleic acid is formed. The methods are particularly suited to high-throughput screening where one or more steps are performed by a computer controlled electromechanical robot comprising an axial rotatable arm and said solid substrate is a portion of a well of a microtiter plate.

5 Claims, No Drawings

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
( A ) LENGTH: 1500 base pairs ( B ) TYPE: nucleic acid
( C ) STRANDEDNESS: double
( D ) TOPOLOGY: linear ( i i ) MOLECULE TYPE: cDNA ( i x ) FEATURE:
( A ) NAME/KEY: CDS
( B ) LOCATION: 1..1500

( x i ) SEQUENCE DESCRIPTION: SEQ ID NO:1:

| ATG | GAC | CAC | ACG | GAG | GGC | TTG | CCC | GCG | GAG | GAG | CCG | CCT | GCG | CAT | GCT | 48 |
|---|---|---|---|---|---|---|---|---|---|---|---|---|---|---|---|---|
| Met | Asp | His | Thr | Glu | Gly | Leu | Pro | Ala | Glu | Glu | Pro | Pro | Ala | His | Ala | |
| 1 | | | | 5 | | | | | 10 | | | | | 15 | | |

| CCA | TCG | CCT | GGG | AAA | TTT | GGT | GAG | CGG | CCT | CCA | CCT | AAA | CGA | CTT | ACT | 96 |
|---|---|---|---|---|---|---|---|---|---|---|---|---|---|---|---|---|
| Pro | Ser | Pro | Gly | Lys | Phe | Gly | Glu | Arg | Pro | Pro | Pro | Lys | Arg | Leu | Thr | |
| | | | 20 | | | | | 25 | | | | | 30 | | | |

| AGG | GAA | GCT | ATG | CGA | AAT | TAT | TTA | AAA | GAG | CGA | GGG | GAT | CAA | ACA | GTA | 144 |
|---|---|---|---|---|---|---|---|---|---|---|---|---|---|---|---|---|
| Arg | Glu | Ala | Met | Arg | Asn | Tyr | Leu | Lys | Glu | Arg | Gly | Asp | Gln | Thr | Val | |
| | | 35 | | | | | 40 | | | | | 45 | | | | |

| CTT | ATT | CTT | CAT | GCA | AAA | GTT | GCA | CAG | AAG | TCA | TAT | GGA | AAT | GAA | AAA | 192 |
|---|---|---|---|---|---|---|---|---|---|---|---|---|---|---|---|---|
| Leu | Ile | Leu | His | Ala | Lys | Val | Ala | Gln | Lys | Ser | Tyr | Gly | Asn | Glu | Lys | |
| | 50 | | | | | 55 | | | | | 60 | | | | | |

| AGG | TTT | TTT | TGC | CCA | CCT | CCT | TGT | GTA | TAT | CTT | ATG | GGC | AGC | GGA | TGG | 240 |
|---|---|---|---|---|---|---|---|---|---|---|---|---|---|---|---|---|
| Arg | Phe | Phe | Cys | Pro | Pro | Pro | Cys | Val | Tyr | Leu | Met | Gly | Ser | Gly | Trp | |
| 65 | | | | | 70 | | | | | 75 | | | | | 80 | |

| AAG | AAA | AAA | AAA | GAA | CAA | ATG | GAA | CGC | GAT | GGT | TGT | TCT | GAA | CAA | GAG | 288 |
|---|---|---|---|---|---|---|---|---|---|---|---|---|---|---|---|---|
| Lys | Lys | Lys | Lys | Glu | Gln | Met | Glu | Arg | Asp | Gly | Cys | Ser | Glu | Gln | Glu | |
| | | | | 85 | | | | | 90 | | | | | 95 | | |

| TCT | CAA | CCG | TGT | GCA | TTT | ATT | GGG | ATA | GGA | AAT | AGT | GAC | CAA | GAA | ATG | 336 |
|---|---|---|---|---|---|---|---|---|---|---|---|---|---|---|---|---|
| Ser | Gln | Pro | Cys | Ala | Phe | Ile | Gly | Ile | Gly | Asn | Ser | Asp | Gln | Glu | Met | |
| | | | 100 | | | | | 105 | | | | | 110 | | | |

| CAG | CAG | CTA | AAC | TTG | GAA | GGA | AAG | AAC | TAT | TGC | ACA | GCC | AAA | ACA | TTG | 384 |
|---|---|---|---|---|---|---|---|---|---|---|---|---|---|---|---|---|
| Gln | Gln | Leu | Asn | Leu | Glu | Gly | Lys | Asn | Tyr | Cys | Thr | Ala | Lys | Thr | Leu | |
| | | | 115 | | | | | 120 | | | | | 125 | | | |

| TAT | ATA | TCT | GAC | TCA | GAC | AAG | CGA | AAG | CAC | TTC | ATT | TTT | TCT | GTA | AAG | 432 |
|---|---|---|---|---|---|---|---|---|---|---|---|---|---|---|---|---|
| Tyr | Ile | Ser | Asp | Ser | Asp | Lys | Arg | Lys | His | Phe | Ile | Phe | Ser | Val | Lys | |
| | | 130 | | | | | 135 | | | | | 140 | | | | |

| ATG | TTC | TAT | GGC | AAC | AGT | GAT | GAC | ATT | GGT | GTG | TTC | CTC | AGC | AAG | CGG | 480 |
|---|---|---|---|---|---|---|---|---|---|---|---|---|---|---|---|---|
| Met | Phe | Tyr | Gly | Asn | Ser | Asp | Asp | Ile | Gly | Val | Phe | Leu | Ser | Lys | Arg | |
| 145 | | | | | 150 | | | | | 155 | | | | | 160 | |

| ATA | AAA | GTC | ATC | TCC | AAA | CCT | TCC | AAA | AAG | AAG | CAG | TCA | TTG | AAA | AAT | 528 |
|---|---|---|---|---|---|---|---|---|---|---|---|---|---|---|---|---|
| Ile | Lys | Val | Ile | Ser | Lys | Pro | Ser | Lys | Lys | Lys | Gln | Ser | Leu | Lys | Asn | |
| | | | | 165 | | | | | 170 | | | | | 175 | | |

| GCT | GAC | TTA | TGC | ATT | GCC | TCA | GGA | ACA | AAG | GTG | GCT | CTG | TTT | AAT | CGA | 576 |
|---|---|---|---|---|---|---|---|---|---|---|---|---|---|---|---|---|
| Ala | Asp | Leu | Cys | Ile | Ala | Ser | Gly | Thr | Lys | Val | Ala | Leu | Phe | Asn | Arg | |
| | | | 180 | | | | | 185 | | | | | 190 | | | |

| CTA | CGA | TCC | CAG | ACA | GTT | AGT | ACC | AGA | TAC | TTG | CAT | GTA | GAA | GGA | GGT | 624 |
|---|---|---|---|---|---|---|---|---|---|---|---|---|---|---|---|---|
| Leu | Arg | Ser | Gln | Thr | Val | Ser | Thr | Arg | Tyr | Leu | His | Val | Glu | Gly | Gly | |
| | | 195 | | | | | 200 | | | | | 205 | | | | |

| AAT | TTT | CAT | GCC | AGT | TCA | CAG | CAG | TGG | GGA | GCC | TTT | TTT | ATT | CAT | CTC | 672 |
|---|---|---|---|---|---|---|---|---|---|---|---|---|---|---|---|---|
| Asn | Phe | His | Ala | Ser | Ser | Gln | Gln | Trp | Gly | Ala | Phe | Phe | Ile | His | Leu | |
| | 210 | | | | | 215 | | | | | 220 | | | | | |

| TTG | GAT | GAT | GAT | GAA | TCA | GAA | GGA | GAA | GAA | TTC | ACA | GTC | CGA | GAT | GGC | 720 |
|---|---|---|---|---|---|---|---|---|---|---|---|---|---|---|---|---|
| Leu | Asp | Asp | Asp | Glu | Ser | Glu | Gly | Glu | Glu | Phe | Thr | Val | Arg | Asp | Gly | |
| 225 | | | | | 230 | | | | | 235 | | | | | 240 | |

| TAC | ATC | CAT | TAT | GGA | CAA | ACA | TGC | AAA | CTT | GTG | TGC | TCA | GTT | ACT | GGC | 768 |
|---|---|---|---|---|---|---|---|---|---|---|---|---|---|---|---|---|
| Tyr | Ile | His | Tyr | Gly | Gln | Thr | Cys | Lys | Leu | Val | Cys | Ser | Val | Thr | Gly | |
| | | | | 245 | | | | | 250 | | | | | 255 | | |

| ATG | GCA | CTC | CCA | AGA | TTG | ATA | ATT | ATG | AAA | GTT | GAT | AAG | CAT | ACC | GCA | 816 |
|---|---|---|---|---|---|---|---|---|---|---|---|---|---|---|---|---|
| Met | Ala | Leu | Pro | Arg | Leu | Ile | Ile | Met | Lys | Val | Asp | Lys | His | Thr | Ala | |
| | | | 260 | | | | | 265 | | | | | 270 | | | |

| | | | | | | | | | | | | | | | | |
|---|---|---|---|---|---|---|---|---|---|---|---|---|---|---|---|---|
| TTA | TTG | GAT | GCA | GAT | GAT | CCT | GTG | TCA | CAA | CTC | CAT | AAA | TGT | GCA | TTT | 864 |
| Leu | Leu | Asp | Ala | Asp | Asp | Pro | Val | Ser | Gln | Leu | His | Lys | Cys | Ala | Phe | |
| | | 275 | | | | | 280 | | | | | 285 | | | | |
| TAC | CTT | AAG | GAT | ACA | GAA | AGA | ATG | TAT | TTG | TGC | CTT | TCT | CAA | GAA | AGA | 912 |
| Tyr | Leu | Lys | Asp | Thr | Glu | Arg | Met | Tyr | Leu | Cys | Leu | Ser | Gln | Glu | Arg | |
| | | 290 | | | | | 295 | | | | | 300 | | | | |
| ATA | ATT | CAA | TTT | CAG | GCC | ACT | CCA | TGT | CCA | AAA | GAA | CCA | AAT | AAA | GAG | 960 |
| Ile | Ile | Gln | Phe | Gln | Ala | Thr | Pro | Cys | Pro | Lys | Glu | Pro | Asn | Lys | Glu | |
| 305 | | | | | 310 | | | | | 315 | | | | | 320 | |
| ATG | ATA | AAT | GAT | GGC | GCT | TCC | TGG | ACA | ATC | ATT | AGC | ACA | GAT | AAG | GCA | 1008 |
| Met | Ile | Asn | Asp | Gly | Ala | Ser | Trp | Thr | Ile | Ile | Ser | Thr | Asp | Lys | Ala | |
| | | | | 325 | | | | | 330 | | | | | 335 | | |
| GAG | TAT | ACA | TTT | TAT | GAG | GGA | ATG | GGC | CCT | GTC | CTT | GCC | CCA | GTC | ACT | 1056 |
| Glu | Tyr | Thr | Phe | Tyr | Glu | Gly | Met | Gly | Pro | Val | Leu | Ala | Pro | Val | Thr | |
| | | | 340 | | | | | 345 | | | | | 350 | | | |
| CCT | GTG | CCT | GTG | GTA | GAG | AGC | CTT | CAG | TTG | AAT | GGC | GGT | GGG | GAC | GTA | 1104 |
| Pro | Val | Pro | Val | Val | Glu | Ser | Leu | Gln | Leu | Asn | Gly | Gly | Gly | Asp | Val | |
| | | 355 | | | | | 360 | | | | | 365 | | | | |
| GCA | ATG | CTT | GAA | CTT | ACA | GGA | CAG | AAT | TTC | ACT | CCA | AAT | TTA | CGA | GTG | 1152 |
| Ala | Met | Leu | Glu | Leu | Thr | Gly | Gln | Asn | Phe | Thr | Pro | Asn | Leu | Arg | Val | |
| | 370 | | | | | 375 | | | | | 380 | | | | | |
| TGG | TTT | GGG | GAT | GTA | GAA | GCT | GAA | ACT | ATG | TAC | AGG | TGT | GGA | GAG | AGT | 1200 |
| Trp | Phe | Gly | Asp | Val | Glu | Ala | Glu | Thr | Met | Tyr | Arg | Cys | Gly | Glu | Ser | |
| 385 | | | | | 390 | | | | | 395 | | | | | 400 | |
| ATG | CTC | TGT | GTC | GTC | CCA | GAC | ATT | TCT | GCA | TTC | CGA | GAA | GGT | TGG | AGA | 1248 |
| Met | Leu | Cys | Val | Val | Pro | Asp | Ile | Ser | Ala | Phe | Arg | Glu | Gly | Trp | Arg | |
| | | | | 405 | | | | | 410 | | | | | 415 | | |
| TGG | GTC | CGG | CAA | CCA | GTC | CAG | GTT | CCA | GTA | ACT | TTG | GTC | CGA | AAT | GAT | 1296 |
| Trp | Val | Arg | Gln | Pro | Val | Gln | Val | Pro | Val | Thr | Leu | Val | Arg | Asn | Asp | |
| | | | 420 | | | | | 425 | | | | | 430 | | | |
| GGA | ATC | ATT | TAT | TCC | ACC | AGC | CTT | ACC | TTT | ACC | TAC | ACA | CCA | GAA | CCA | 1344 |
| Gly | Ile | Ile | Tyr | Ser | Thr | Ser | Leu | Thr | Phe | Thr | Tyr | Thr | Pro | Glu | Pro | |
| | | 435 | | | | | 440 | | | | | 445 | | | | |
| GGG | CCA | CGG | CCA | CAT | TGC | AGT | GTA | GCA | GGA | GCA | ATC | CTT | CCA | GCC | AAT | 1392 |
| Gly | Pro | Arg | Pro | His | Cys | Ser | Val | Ala | Gly | Ala | Ile | Leu | Pro | Ala | Asn | |
| | 450 | | | | | 455 | | | | | 460 | | | | | |
| TCA | AGC | CAG | GTG | CCC | CCT | AAC | GAA | TCA | AAC | ACA | AAC | AGC | GAG | GGA | AGT | 1440 |
| Ser | Ser | Gln | Val | Pro | Pro | Asn | Glu | Ser | Asn | Thr | Asn | Ser | Glu | Gly | Ser | |
| 465 | | | | | 470 | | | | | 475 | | | | | 480 | |
| TAC | ACA | AAC | GCC | AGC | ACA | AAT | TCA | ACC | AGT | GTC | ACA | TCA | TCT | ACA | GCC | 1488 |
| Tyr | Thr | Asn | Ala | Ser | Thr | Asn | Ser | Thr | Ser | Val | Thr | Ser | Ser | Thr | Ala | |
| | | | | 485 | | | | | 490 | | | | | 495 | | |
| ACA | GTG | GTA | TCC | | | | | | | | | | | | | 1500 |
| Thr | Val | Val | Ser | | | | | | | | | | | | | |
| | | | 500 | | | | | | | | | | | | | |

( 2 ) INFORMATION FOR SEQ ID NO:2:

( i ) SEQUENCE CHARACTERISTICS:
        ( A ) LENGTH: 500 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| | | | | | | | | | | | | | | | |
|---|---|---|---|---|---|---|---|---|---|---|---|---|---|---|---|
| Met | Asp | His | Thr | Glu | Gly | Leu | Pro | Ala | Glu | Pro | Pro | Ala | His | Ala | |
| 1 | | | | 5 | | | | | 10 | | | | | 15 | |
| Pro | Ser | Pro | Gly | Lys | Phe | Gly | Glu | Arg | Pro | Pro | Lys | Arg | Leu | Thr | |
| | | | 20 | | | | | 25 | | | | | 30 | | |
| Arg | Glu | Ala | Met | Arg | Asn | Tyr | Leu | Lys | Glu | Arg | Gly | Asp | Gln | Thr | Val |
| | | | 35 | | | | | 40 | | | | | 45 | | |

Leu Ile Leu His Ala Lys Val Ala Gln Lys Ser Tyr Gly Asn Glu Lys
 50                  55                      60

Arg Phe Phe Cys Pro Pro Pro Cys Val Tyr Leu Met Gly Ser Gly Trp
 65              70                  75                       80

Lys Lys Lys Lys Glu Gln Met Glu Arg Asp Gly Cys Ser Glu Gln Glu
             85                  90                      95

Ser Gln Pro Cys Ala Phe Ile Gly Ile Gly Asn Ser Asp Gln Glu Met
            100             105                 110

Gln Gln Leu Asn Leu Glu Gly Lys Asn Tyr Cys Thr Ala Lys Thr Leu
        115                 120                 125

Tyr Ile Ser Asp Ser Asp Lys Arg Lys His Phe Ile Phe Ser Val Lys
    130             135                 140

Met Phe Tyr Gly Asn Ser Asp Asp Ile Gly Val Phe Leu Ser Lys Arg
145             150                 155                     160

Ile Lys Val Ile Ser Lys Pro Ser Lys Lys Lys Gln Ser Leu Lys Asn
                165             170                     175

Ala Asp Leu Cys Ile Ala Ser Gly Thr Lys Val Ala Leu Phe Asn Arg
            180             185                 190

Leu Arg Ser Gln Thr Val Ser Thr Arg Tyr Leu His Val Glu Gly Gly
        195                 200                 205

Asn Phe His Ala Ser Ser Gln Gln Trp Gly Ala Phe Phe Ile His Leu
210                 215                 220

Leu Asp Asp Asp Glu Ser Glu Gly Glu Glu Phe Thr Val Arg Asp Gly
225                 230                 235                 240

Tyr Ile His Tyr Gly Gln Thr Cys Lys Leu Val Cys Ser Val Thr Gly
                245                 250                 255

Met Ala Leu Pro Arg Leu Ile Ile Met Lys Val Asp Lys His Thr Ala
            260                 265                 270

Leu Leu Asp Ala Asp Asp Pro Val Ser Gln Leu His Lys Cys Ala Phe
        275                 280                 285

Tyr Leu Lys Asp Thr Glu Arg Met Tyr Leu Cys Leu Ser Gln Glu Arg
    290                 295                 300

Ile Ile Gln Phe Gln Ala Thr Pro Cys Pro Lys Glu Pro Asn Lys Glu
305                 310                 315                 320

Met Ile Asn Asp Gly Ala Ser Trp Thr Ile Ile Ser Thr Asp Lys Ala
                325                 330                 335

Glu Tyr Thr Phe Tyr Glu Gly Met Gly Pro Val Leu Ala Pro Val Thr
            340                 345                 350

Pro Val Pro Val Val Glu Ser Leu Gln Leu Asn Gly Gly Gly Asp Val
        355                 360                 365

Ala Met Leu Glu Leu Thr Gly Gln Asn Phe Thr Pro Asn Leu Arg Val
370                 375                 380

Trp Phe Gly Asp Val Glu Ala Glu Thr Met Tyr Arg Cys Gly Glu Ser
385                 390                 395                 400

Met Leu Cys Val Val Pro Asp Ile Ser Ala Phe Arg Glu Gly Trp Arg
                405                 410                 415

Trp Val Arg Gln Pro Val Gln Val Pro Val Thr Leu Val Arg Asn Asp
            420                 425                 430

Gly Ile Ile Tyr Ser Thr Ser Leu Thr Phe Thr Tyr Thr Pro Glu Pro
        435                 440                 445

Gly Pro Arg Pro His Cys Ser Val Ala Gly Ala Ile Leu Pro Ala Asn
450                 455                 460

Ser Ser Gln Val Pro Pro Asn Glu Ser Asn Thr Asn Ser Glu Gly Ser 465            470                475                480
Tyr Thr Asn Ala Ser Thr Asn Ser Thr Ser Val Thr Ser Ser Thr Ala
                485                490                495
Thr Val Val Ser
         500

( 2 ) INFORMATION FOR SEQ ID NO:3:

( i ) SEQUENCE CHARACTERISTICS:
        ( A ) LENGTH: 28 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:3:

GGAAACACGC CGTGGGAAAA AATTTGGC                                              28

( 2 ) INFORMATION FOR SEQ ID NO:4:

( i ) SEQUENCE CHARACTERISTICS:
        ( A ) LENGTH: 28 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:4:

GGAAACACGC CGTGGCTAAA AATTTGGG                                              28

( 2 ) INFORMATION FOR SEQ ID NO:5:

( i ) SEQUENCE CHARACTERISTICS:
        ( A ) LENGTH: 28 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:5:

TCCTTCAGCC CTGTGGGAAC TTGCTGCT                                              28

( 2 ) INFORMATION FOR SEQ ID NO:6:

( i ) SEQUENCE CHARACTERISTICS:
        ( A ) LENGTH: 28 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:6:

GGACTACCAC TGTGGGATCC TCTGGAGG                                              28

( 2 ) INFORMATION FOR SEQ ID NO:7:

( i ) SEQUENCE CHARACTERISTICS:
        ( A ) LENGTH: 28 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:7:

```
GGACTACCAC TGTGCCTTCC TCTGGAGG                                                                    28
```

( 2 ) INFORMATION FOR SEQ ID NO:8:

( i ) SEQUENCE CHARACTERISTICS:
        ( A ) LENGTH: 42 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:8:

```
CAAGAGACAG AGTTTCTAAG CTTATTGTAA TTTTAAGCAT CG                                                     42
```

( 2 ) INFORMATION FOR SEQ ID NO:9:

( i ) SEQUENCE CHARACTERISTICS:
        ( A ) LENGTH: 28 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:9:

```
AAGCATCGTG GATATTCCCG GCACAGCT                                                                    28
```

( 2 ) INFORMATION FOR SEQ ID NO:10:

( i ) SEQUENCE CHARACTERISTICS:
        ( A ) LENGTH: 28 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:10:

```
TATATGCCCG GGAAAGTTTT TGTATTCC                                                                    28
```

( 2 ) INFORMATION FOR SEQ ID NO:11:

( i ) SEQUENCE CHARACTERISTICS:
        ( A ) LENGTH: 28 base pairs
        ( B ) TYPE: nucleic acid
        ( C ) STRANDEDNESS: double
        ( D ) TOPOLOGY: linear ( i i ) MOLECULE TYPE: cDNA ( x i ) SEQUENCE DESCRIPTION: SEQ ID NO:11:

```
GATGCCATTG GGGATTTCCT CTTTACTG                                                                    28
```

EPSTEIN-BARR VIRUS TRANSCRIPTION FACTOR BINDING ASSAY

CROSS-REFERENCE TO RELATED APPLICATIONS

This application is a continuation of application Ser. No. 08/246,977, filed May 20, 1994, now abandoned.

INTRODUCTION

1. Field of the Invention

The field of this invention is assays for screening for drugs which interfere with sequence-specific protein-DNA binding.

2. Background

In most populations 90–95% of adults reveal evidence of Epstein Barr virus (EBV) infection. Infection generally occurs early in life (age <6 years) and is largely asymptomatic. Infection of college bound adults (approx. 1% per year) results in infectious mononucleosis in 30–45% of the infected individuals. IM is usually a self-limiting lymphoproliferative disease characterized by fever, malaise, and fatigue, which is rarely fatal. EBV infection is also involved in Burkitt's lymphoma prevalent in East Africa and nasopharyngeal carcinoma prevalent in Southeast Asia.

The population at risk worldwide for the development of fatal EBV-associated lymphoproliferative disorders are individuals that are immunologically compromised because of immunosuppressive therapy or AIDS. The incidence of EBV infection and associated lymphoproliferative disorders in transplant patients is 40%, with 1% of the renal transplant and 5% of the heart transplant patients progressing to develop lymphomas. EBV-associated disease is also prevalent among AIDS patients. Effective therapeutics are entirely unavailable for EBV disease. Therapy for infectious mononucleosis is usually symptomatic and bed rest. Acyclovir has minimal effects on infectious mononucleosis symptoms or on the treatment of lymphoproliferative disorders in immunocompromised hosts.

Identifying and developing new pharmaceuticals is a multibillion dollar industry in the U.S. alone. Urgently needed are efficient methods of identifying pharmacological agents or drugs which are active at the level of gene transcription. If amenable to automated, cost-effective, high throughput drug screening, such methods would have immediate application in a broad range of domestic and international pharmaceutical and biotechnology drug development programs.

Gene-specific transcription factors provide a promising class of targets for novel therapeutics directed to EBV diseases. For example, production of virus particles and spread of the virus occurs during the lyric phase; an agent that blocks this phase would block spread of the virus and may be beneficial for treatment of infectious mononucleosis. The virus employs the latent mode of replication for persistence in humans and an inhibitor of this phase of the life cycle would lead to elimination of the virus from the body.

One viral encoded transcription factor, Epstein-Barr virus Nuclear Antigen 2 (EBNA2) appears critical for both EBV B-cell immortalization and establishment of latency (3, 4). EBNA2 transactivates latent vital genes as well as certain cellular genes that have been implicated in B-cell activation (5–10). EBNA2, activates gene expression through a common cis-regulatory element found in both viral and cellular promoters (11). EBNA2 appears unable to bind directly to these regulatory elements. In vitro experiments suggested EBNA2 requires an activity in a host cell extract, termed C-promoter binding factor 1 (CBF1) activity, to associate with its target genes.

Since the binding of EBNA2 to both viral promoters and the promoters of B-cell activation genes is dependent upon CBF1 activity, we sought to identify a biomolecule(s) responsible for this activity. The identification and characterization of such a biomolecule might permit its manufacture for use in commercial pharmaceutical screening assays.

Relevant Literature

Preliminary identification of a CBF1 activity is reported in P. D. Ling, D. R. Rawlins, S. D. Hayward, *Proc. Natl. Acad. Sci. USA* 90, 9237–9241 (1993) and P. D. Ling, J. I. Ryon, S. D. Hayward, *J. Virol.* 67, 2990–3003 (1993).

Cloning of murine and human RBPJK is reported in N. Matsunami, et al., *Nature* 342, 934–937 (1989) and R. Amakawa, et al., *Genomics* 17, 306–315 (1993).

SUMMARY OF THE INVENTION

The invention provides methods and compositions for identifying pharmacological agents useful in the diagnosis or treatment of disease associated with the expression of a gene modulated by a transcription complex containing at least CBF1 and a transcription factor.

In general, the methods involve combining a first polypeptide comprising a portion of CBF1 capable of selectively binding a portion of a transcription factor such as the Epstein-Barr virus EBNA2, a second polypeptide comprising that portion of that transcription factor, and a candidate pharmacological agent. The resultant mixture is incubated under conditions whereby, but for the presence of the candidate pharmacological agent, the first polypeptide selectively binds the second polypeptide. Then the presence or absence of selective binding between the first and second polypeptides is detected; where the absence of selective binding indicates that the candidate pharmacological agent is capable of selectively modulating the expression of a gene dependent on CBF1-transcription factor binding. As exemplified by EBNA2, such an agent is useful in the diagnosis or treatment of disease associated with the expression of the gene.

Alternatively, the mixture may further comprise a nucleic acid comprising a CBF1 binding sequence including the nucleotide sequence: G-G-G-A, preferably, C-G-T-G-G-G-A-A. This mixture is incubated under conditions whereby, but for the presence of the candidate pharmacological agent, a transcription complex comprising both polypeptides bound, directly or indirectly to the nucleic acid is formed. The presence or absence of transcription complex formation is then detected.

A wide variety of alternative embodiments of the general methods using CBF1 portion containing polypeptides are disclosed. These encompass a variety of genes, transcription factors and methods for isolating and detecting polypeptides and transcription complexes, e.g. ligand tagging followed by immobilized receptor isolation, direct labels, specific binding labels, etc. The methods are particularly suited to high-throughput screening where one or more steps are performed by a computer controlled electromechanical robot comprising an axial rotatable arm and said solid substrate is a portion of a well of a microtiter plate.

In a specific embodiment, the methods involve combining the first polypeptide, a labelled form of the second polypeptide, the candidate pharmacological agent, a receptor immobilized on a solid substrate such as a microliter plate and the nucleic acid conjugated to a ligand capable of specifically binding the receptor. The resultant mixture is incubated under conditions whereby the receptor is bound to the ligand and, but for the presence of the candidate pharmacological agent, the first polypeptide is sequence-specifically bound to the nucleic acid conjugate and the labelled second polypeptide is selectively bound to the first polypeptide. Labelled polypeptide that is not sequence-specifically bound to the nucleic acid conjugate through the first polypeptide is removed and/or washed from the solid substrate and labelled polypeptide which is sequence-specifically bound to the conjugate through the first polypeptide is detected. Binding reactions which include candidate agents which disrupt transcription factor formation retain less label on the substrate and so yield diminished label signal.

DETAILED DESCRIPTION OF THE INVENTION

The invention provides efficient methods of identifying pharmacological agents or drugs which are active at the level of CBF1-dependent gene transcription. The methods are amenable to automated, cost-effective high throughput drug screening and have immediate application in a broad range of domestic and international pharmaceutical and biotechnology drug development programs.

Target diseases are limited only in that disease or disease progression be subject to inhibition by alteration of the formation of a transcription complex comprising CBF1 and/or its specific interaction with a gene or gene regulatory region. Since progression of wide variety of diseases requires CBF1-dependent gene transcription, target diseases include viral, bacterial and fungal infections, metabolic disease, genetic disease, cell growth and regulatory disfunction, such as neoplasia, inflammation, hypersensitivity, etc. The target diseases may be afflictions of plants, especially agricultural crops, or animals, especially livestock, house animals and humans.

CBF1-dependent gene transcription is modulated by altering the formation or function of transcription complexes comprising CBF1. Such complexes often comprise one or more transcription factors capable of sequence-specific interaction with a portion of a gene or gene regulatory region. This interaction may be direct sequence-specific binding where the transcription factor directly contacts the nucleic acid or indirect sequence-specific binding mediated or facilitated by CBF1 or other auxiliary proteins where the transcription factor is tethered to the nucleic acid by a direct nueleic acid binding protein, such as CBF1. In addition, some transcription factors demonstrate induced or synergistic binding, i.e. the affinity or specificity of the DNA binding is enhanced in the presence of another protein like CBF1.

A preferred class of transcription complexes comprise CBF1 and EBV EBNA2 or one of the EBNA2 cellular homologs. EBNA2 cellular homologs generally exhibit selective CBF1 binding of at least about $10^6M^{-1}$, preferably at least about $10^8M^{-1}$ and CBF1 transcriptional dependency. EBNA2 homologs have at least two domains—one that interacts with CBF1 and another that interacts with other transcription proteins such as TAFs. These proteins are readily identified in functional assays such as gel shifts or transcription assay using CBF1 cis elements.

Preferred EBNA2 homologs and their coding sequences share substantial sequence similarity. "Substantial sequence identity" or "substantially homologous" means that respective portions, preferably the CBF1 binding portions, of the polypeptides present at least about 20%, more preferably at least about 40%, and most preferably at least about 80% sequence identity. Where the sequence diverge, the differences are preferably conservative, i.e. an acidic for an acidic amino acid substitution or a nucleotide change providing a redundant codon. Dissimilar sequences are typically aggregated within regions rather than being distributed evenly over the portions. Substantially identical or homologous sequences hybridize to their respective complements under low stringency conditions, for example, at 50° C. and SSC (0.9M saline/0.09M sodium citrate) and remain bound when subject to washing at 55° C. with SSC.

The disclosed methods and kits involve reconstituting, in vitro, CBF1, a CBF1 dependent transcription factor, and/or nucleic acid interactions, and challenging the reconstitution with candidate therapeutics. Preferred applications of the method include gene transcriptional regulation where at least one transcription factor other than CBF1 has been molecularly cloned.

In one embodiment, the methods involve forming a mixture by combining a first polypeptide comprising or consisting essentially of a portion of CBF1 capable of selectively binding a portion of a transcription factor such as the Epstein-Barr virus EBNA2, a second polypeptide comprising that portion of that transcription factor, and a candidate pharmacological agent. The polypeptides are usually added in an isolated, partially pure or pure form and are typically recombinantly produced. As used herein, an "isolated" polypeptide or nucleic acid is unaccompanied by at least some of the material with which it is associated in its natural state and constitutes at least about 0.5%, preferably at least about 2%, and more preferably at least about 5% by weight of the total protein in a given sample; a partially pure polypeptide constitutes at least about 10%, preferably at least about 30%, and more preferably at least about 60% by weight of the total protein in a given sample; and a :pure polypeptide constitutes at least about 70% , preferably at least about 90%, and more preferably at least about 95% by weight of the total protein in a given sample.

The portions are usually at least about 20, more usually at least about 40, most usually at least about 80 amino acids in length and include residues sufficient to provide the protein with CBF1 or transcription factor-specificity similar to that of the native transcription factor. For example, a CBF1 portion containing polypeptide comprises at least 50, preferably at least 100, more prefereably at least 200, most preferably at least about 400 amino acids of the CBF1 amino acid sequence. Frequently, the polypeptides comprise full-length or substantially full-length (at least 75%, preferably at least 85%, more perferably at least 90%, most preferably at least 95%) CBF1 and/or transcription factor. The polypeptides are capable of binding each other with an equilibrium constant at least about $10^4M^{-1}$, preferably at least about $10^6M^{-1}$, more preferably at least about $10^8M^{-1}$ and not less than six, preferably not less than four, more preferably not less than two orders of magnitude less than the binding equilibrium constant of full-length CBF1 with the native transcription factor under similar conditions.

Preferred CBF1 and transcription factor portions capable of imparting the requisite binding specificity and affinity are readily identified by those skilled in the art. A wide variety of molecular and biochemical methods are available for generating preferred portions, see e.g. Molecular Cloning, A Laboratory Manual (2nd Ed., Sambrook, Fritsch and Maniatis, Cold Spring Harbor), Current Protocols in Molecular Biology (Eds. Aufubel, Brent, Kingston, More, Feidman, Smith and Stuhl, Greene Publ. Assoc., Wiley- Interscience, NY, N.Y., 1992) or that are otherwise known in the art. For example, deletion mutants are screened for selective protein or sequence-specific binding directly using binding assays including those described herein or other assays such as electrophoretic mobility shift analysis (EMSA). The proteins may comprise additional components depending upon the assay reagents and conditions. For example, it may be desirable that the protein be a fusion product of the transcription factor portion and another polypeptide, e.g. a polypeptide that is capable of providing or enhancing protein-protein binding, sequence-specific nucleic acid binding or stability under assay conditions (e.g. a tag for detection or anchoring).

The mixture often additionally comprises a nucleic acid comprising at least a CBF1 binding sequence which shares sufficient sequence similarity with a gene or gene regulatory region to which native CBF1 naturally binds to provide sequence-specific binding of the CBF1 portion containing polypeptide. Frequently, the nucleic acid further comprises one or more sequences which facilitate the binding of the transcription factor portion polypeptide or further facilitate the formation of a bound transcription complex. Thus, the nucleic acid frequently comprises a sequence which shares sufficient sequence similarity with a gene or gene regulatory region to which the native CBF1-dependent transcription factor normally binds.

Binding site portions of the nucleic acid constitute at least about 4, preferably at least about 6, more preferably at least about 8 nucleotides. Nucleic acids comprising a CBF1 binding site include the nucleotide sequence: G-G-G-A, preferably the sequence: GTGGGAAA. Binding sequences for other transcription factors may be found in sources such as the Transcription Factor Database of the National Center for Biotechnology Information at the National Library for Medicine, in Faisst and Meyer (1991) Nucleic Acids Research 20, 3-26, and others known to those skilled in this art.

The nucleic acid portion bound by the polypeptide(s) may be continuous or segmented. Additional nucleotides may used to provide structure which enhances or decreased binding or stability, etc. For example, combinatorial DNA binding can be effected by including two or more DNA binding sites for different or the same transcription factor cm the oligonucleotide. This allows for the study of cooperative or synergistic DNA binding of two or more factors. In addition, the nucleic acid can comprise a cassette into which transcription factor binding sites are conveniently spliced fix use in the subject assays.

The nucleic acid is usually linear and double-stranded DNA, though circular plasmids or other nucleic acids or structural analogs may be substituted so long as CBF1 sequence-specific binding is retained. In some applications, supercoiled DNA provides optimal sequence-specific binding and is preferred. The nucleic acid is often recombinant, meaning it comprises a sequence joined to a nucleotide other than that which it is joined to on a natural chromosome. An isolated nucleic acid nucleotide sequence constitutes at least about 0.5%, preferably at least about 2%, and more preferably at least about 5% by weight of total nucleic acid present in a given fraction. A partially pure nucleotide sequence constitutes at least about 10% , preferably at least about 30%, and more preferably at least about 60% by weight of total nucleic acid present in a given fraction. A pure nucleotide sequence constitutes at least about 80%, preferably at least about 90%, and more preferably at least about 95% by weight of total nucleic acid present in a given fraction. The nucleic acid may be of any length amenable to the assay conditions and requirements. Typically the nucleic acid is between 8 bp and 5 kb, preferably between about 12 bp and 1 kb, more preferably between about 18 bp and 250 bp, most preferably between about 27 and 50 bp.

The mixture also comprises a candidate pharmacological agent. Candidate agents encompass numerous chemical classes, though typically they are organic compounds; preferably small organic compounds. Small organic compounds have a molecular weight of more than 50 yet less than about 2,500, preferably less than about 1000, more preferably, less than about 500. Candidate agents comprise functional chemical groups necessary for structural interactions with proteins and/or DNA, and typically include at least an amine, carbonyl, hydroxyl or carboxyl group, preferably at least two of said functional chemical groups, more preferably at least three. The candidate agents often comprise cyclical carbon or heterocyclic structures and/or aromatic or polyaromatic structures substituted with one or more of the forementioned functional groups. Candidate agents are also found among biomolecules including peptides, saccharides, fatty acids, steroids, purines, pyrimidines, derivatives, structural analogs or combinations thereof, and the like.

Candidate agents are obtained from a wide variety of sources including libraries of synthetic or natural compounds. For example, numerous means are available for random and directed synthesis of a wide variety of organic compounds and biomolecules, including expression of randomized oligonucleotides. Alternatively, libraries of natural compounds in the form of bacterial, fungal, plant and animal extracts are available or readily produced. Additionally, natural and synthetically produced libraries and compounds are readily modified through conventional chemical, physical, and biochemical means. In addition, known pharmacological agents may be subject to directed or random chemical modifications, such as acylation, alkylation, esterification, amidification, etc., to produce structural analogs.

A variety of other reagents may also be included in the mixture. These include reagents like salts, buffers, neutral proteins, e.g. albumin, detergents, etc. which may be used to facilitate optimal protein-protein and/or protein-nucleic acid binding and/or reduce non-specific or background interactions, etc. Also, reagents that otherwise improve the efficiency of the assay, such as protease inhibitors, nuclease inhibitors, antimicrobial agents, etc. may be used.

The resultant mixture is incubated under conditions whereby, but for the presence of the candidate pharmacological agent, the first polypeptide selectively binds the second polypeptide. The mixture components can be added in any order that provides for the requisite bindings. Incubations may be performed at any temperature which facilitates optimal binding, typically between 4° and 40° C., more commonly between 15° and 40° C. Incubation periods are likewise selected for optimal binding but also minimized to facilitate rapid, high-throughput screening, and are typically between 0.1 and 10 hours, preferably less than 5 hours, more preferably less than 2 hours.

After incubation, the presence or absence of selective binding between the first and second polypeptides is detected by any convenient way. Often, a separation step is used to separate bound from unbound proteins. The seperation step may be accomplished in a variety of ways. Conveniently, at least one of the proteins is immobilized on a solid substrate which may be any solid from which the unbound protein may be conveniently separated. The solid substrate may be made of a wide variety of materials and in a wide variety of shapes, e.g. microliter plate, microbead, dipstick, resin particle, etc. The substrate is chosen to maximize signal to noise ratios, primarily to minimize background binding, for ease of washing and cost.

Separation may be effected for example, by removing a bead or dipstick from a reservoir, emptying or diluting reservoir such as a microtiter plate well, rinsing a bead (e.g. beads with iron cores may be readily isolated and washed using magnets), particle, chromatographic column or filter with a wash solution or solvent. Typically, the separation step will include an extended rinse or wash or a plurality of rinses or washes. For example, where the solid substrate is a microtiter plate, the wells may be washed several times with a washing solution, which typically includes those components of the incubation mixture that do not participate in specific binding such as salts, buffer, detergent, nonspecific protein, etc. may exploit a polypeptide specific binding reagent such as an antibody or receptor specific to a ligand of the polypeptide.

Detection may be effected in any convenient way. Frequently, one of the proteins comprises or is coupled to a label. A wide variety of labels may be employed— essentially any label that provides for detection of bound protein. The label may provide for direct detection as radioactivity, luminescence, optical or electron density, etc. or indirect detection such as an epitope tag, an enzyme, etc. The label may be appended to the protein e.g. a phosphate group comprising a radioactive isotope of phosphorous, or incorporated into the protein structure, e.g. a methionine residue comprising a radioactive isotope of sulfur.

A variety of methods may be used to detect the label depending on the nature of the label and other assay components. For example, the label may be detected bound to the solid substrate or a portion of the bound complex containing the label may be separated from the solid substrate, and thereafter the label detected. Labels may be .directly detected through optical or electron density, radiative emissions, nonradiative energy transfers, etc. or indirectly detected with antibody conjugates, etc. For example, in the case of radioactive labels, emissions may be detected directly, e.g. with particle counters or indirectly, e.g. with scintillation cocktails and counters. Candidate agents shown to inhibit protein-protein binding or transcription complex formation provide valuable reagents to the pharmaceutical and agricultural industries for cellular, plant, field crop, animal and human trials.

The methods are particularly suited to automated high throughput drug screening. In a preferred embodiment, the individual sample incubation volumes are less than about 500 ul, preferably less than about 250 ul, more preferably less than about 100 ul. Such small sample volumes minimize the use of often scarce candidate agent, expensive transcription complex components, and hazardous radioactive waste. Furthermore, the methods provide for automation, especially computerized automation. Accordingly, the method steps are preferably performed by a computer-controlled electromechanical robot. While individual steps may be separately automated, a preferred embodiment provides a single computer-controlled multifunction robot with a single arm axially rotating to and from a plurality of work stations performing the mixture forming, incubating and separating steps. The computer is loaded with software which provides the instructions which direct the arm and work station operations and provides input (e.g. keyboard and/or mouse) and display (e.g. monitor) means for operator interfacing.

In another embodiment, the methods involve combining the first CBF1 portion containing polypeptide, a labelled form of the second transcription factor portion containing polypeptide, the candidate pharmacological agent, a receptor immobilized on a solid substrate and the nucleic acid conjugated to a ligand capable of specifically binding the receptor.

The labelled protein comprises a label that provides for detection of the labelled protein when complexed, usually through the CBF1 portion protein, to the nucleic acid conjugate. The nucleic acid conjugate comprises a nucleic acid, as previously described, coupled to a ligand. The ligand of the nucleic acid conjugate is capable of specifically binding the immobilized receptor. The ligand-receptor binding is specific enough to provide a maximized and at least measurable signal to noise ratio (receptor mediated vs. non-specific retention of the label on the substrate). The nucleic acid conjugate is typically capable of binding the receptor with an affinity of at least about $10^5 M^{-1}$, preferably at least about $10^6 M^{-1}$, more preferably at least about $10^8 M^{-1}$. In a preferred embodiment, a plurality of ligands are capable of binding each receptor. Exemplary ligand-receptor pairs include biotin and avidin, antigen and antibody, sugar and lectin, ion and chelator, etc.

As above, the mixture usually includes additional reagents to facilitate optimal receptor-ligand and protein-nucleic acid binding or to reduce non-specific or background protein-substrate, nucleic acid-substrate, protein-protein and protein-DNA interactions, etc. The mixture is incubated under conditions whereby the receptor is bound to the ligand and, but for the presence of the candidate pharmacological agent, the first polypeptide is sequence-specifically bound to the nucleic acid conjugate and the labelled second polypeptide is selectively bound to the first polypeptide. Incubations are as previously described. After receptor-ligand and protein-nucleic acid binding have occurred, a fraction comprising labelled protein which is not directly or, as is usually the case, sequence-specifically bound through the CBF1 polypeptide is separated from the solid substrate. This step may be accomplished in a variety of ways as described above. After separating the unbound fraction from the solid substrate, the presence of bound nucleic acid-protein complex is detected via the labeled protein.

As previously described, the methods are particularly suited to automated high throughput drug screening. In a particular embodiment, the arm retrieves and transfers a microtiter plate to a liquid dispensing station where measured aliquots of each an incubation buffer and a solution comprising one or more candidate agents are deposited into each designated well. The arm then retrieves and transfers to and deposits in designated wells a measured aliquot of a solution comprising a labeled transcription factor protein. After a first incubation period, the liquid dispensing station deposits in each designated well a measured aliquot of a biotinylated nucleic acid solution. The first and/or following second incubation may optionally occur after the arm transfers the plate to a shaker station. After a second incubation period, the arm transfers the microliter plate to a wash station where the unbound contents of each well is aspirated and then the well repeatedly filled with a wash buffer and aspirated. Where the bound label is radioactive phosphorous, the arm retrieves and transfers the plate to the liquid dispensing station where a measured aliquot of a scintillation cocktail is deposited in each designated well. Thereafter, the amount of label retained in each designated well is quantified.

In more preferred embodiments, the liquid dispensing station and arm are capable of depositing aliquots in at least eight wells simultaneously and the wash station is capable of filling and aspirating ninety-six wells simultaneously. Preferred robots are capable of processing at least 640 and preferably at least about 1,280 candidate agents every 24 hours, e.g. in microtiter plates. Of course, useful agents are identified with a range of other assays (e.g. gel shifts, etc.) employing CBF1 portion containing protein.

EXPERIMENTAL

The existence of a CBF1 activity was initially suggested based on experiments with an extract isolated from B-cells (11). To investigate the feasibility of identifying and characterizing a CBF1-like activity, we first sought to determine whether there existed a cellular source of CBF1-like activity suitable for purification purposes. We ultimately identified HeLa cells as a source of CBF1-like activity. We used gel mobility shift assays comparing extracts from various cell types to demonstrate that HeLa cells contain a C-promoter binding activity similar to CBF1. The HeLa cell bandshift is supershifted by native EBNA2, but not by the EBNA2WW mutant.

Our HeLa CBF1 was purified from cells using Heparin-sepharose chromatography, followed by DNA-affinity chromatography on the C-promoter binding site. Briefly, HeLa cells ($5\times10^{10}$) were extracted (20) and chromatographed on wheat germ agglutinin (WGA) (21) as described previously. The CBF1 activity was precipitated from the WGA flow through by adding ammonium sulfate to 55%. The pellet was resuspended in and dialyzed into 0.275M KCl in 25 mM Hepes pH 7.9, 0.5 mM EDTA, 20% glycerol, 1 mM dithiothreitol, 0.1% AEBSF, 0.1% NaMetabisulfite, 0.05% LDAO (HEG), then applied to Heparin-sepharose (5 mg/ml) equilibrated in the same buffer. CBF1 activity was step eluted with 0.375M KCl HEG, polydIC was added to 25 ug/ml and then applied directly to a DNA affinity column equilibrated in the same buffer. The DNA-affinity resin consisted of a double-stranded C-promoter EBNA2 responsive element (SEQ ID NO: 3) via a 5' end biotin on the sense strand to avidin-agarose (0.5 mg oligo/ml avidin-agarose). Bound proteins were washed with 2 column volumes of 0.375M KCl KEG containing 500 ug/ml double-stranded C-promoter EBNA2 responsive element containing a double point mutation (SEQ ID NO: 4). CBF1 activity was step eluted with 0.6M KCl HEG. DNA-affinity chromatography was repeated omitting protease inhibitors.

Our CBF1 activity appeared to derive from a 60 KD polypeptide and a minor polypeptide that migrated slightly slower on denaturing polyacrylamide gels. Both of these polypeptides copurified with CBF1 binding activity as determined by bandshift analysis using a C-promoter recognition site and supershift analysis with EBNA2. Purified CBF1 was digested with trypsin, and the resulting peptides were purified by reverse-phase HPLC. The peptide sequences showed that CBF1 is nearly identical to a previously characterized protein, termed recombination binding protein of J kappa (13, 14) (RBPJK). A single difference between the RBPJK sequence (14) and our CBF1 (determined on 6 independent PCR products) is at amino acid 240 (V to G). A glycine is found at this position in both the mouse and Drosophila sequences.

To test whether RBPJK has CBF1 activity, we cloned its cDNA SEQ ID NO: 1 and expressed the 500 amino acid coding region SEQ ID NO: 2 both in human 293 cells and reticulocyte lysates. Although 293 cells contain endogenous CBF1, transient expression of RBPJK under the control of the strong CMV promoter resulted in an increased level of CBF1 binding activity. Likewise, reticulocyte lysates programmed with RBPJK mRNA yield a bandshift on the C-promoter site that co-migrates with that produced by CBF1. That these RBPJK specified bandshift activities function in the same way as purified CBF1 was confirmed by their ability to form an EBNA2 supershifted complex. These data indicate that CBF1 and RBPJK are one and the same.

Since EBNA2 is incapable of binding to the Cp site alone, we reasoned that EBNA2 might be tethered to its target genes via direct protein-protein interactions with CBF1. If so, CBF1 and EBNA2 might be capable of interacting in solution. To test this hypothesis, we translated CBF1 in the presence of $^{35}$s methionine and then assayed for specific binding to affinity resins containing various GST fusion proteins. Radiolabelled CBF1 bound to GST-EBNA2, but not to GST-EBNA2WW (mutant that is unable to supershift the CBF1/DNA complex), nor two other protein controls. These observations indicate that CBF1 interacts specifically with EBNA2 and that this interaction can occur in the absence of DNA.

RBPJK was originally characterized as a protein that binds to the recombination signal sequence of the J kappa gene that is required for V(D)J recombination (13). The signal sequence is composed of heptamer (CACTGTG) and nonamer (GGTTTTTGT) motifs separated by a nonconserved spacer. Using bandshift and footprint analysis, RBPJK was found to bind the heptamer sequence (15), and has thus been proposed to be involved in immunoglobulin gene recombination. The heptamer sequence bears little resemblance to the conserved core of the EBNA2 responsive element (GTGGGAAA) that is critical for CBF1 binding. However, upon inspecting the DNA probes that were used for the RBPJK experiments, we noticed that the heptamer site was positioned adjacent to a BamHI linker sequence so as to create the sequence GTGGGA which is a close match to the CBF1 consensus sequence.

In order to investigate whether this artificial site is capable of binding CBF1, we tested the various potential CBF1 binding sites as competitors in a bandshift assay, using the C-promoter site as a probe. To set the range for competitor sites we first compared a mutant severely defective in CBF1 binding with the native C-promoter site that contains a consensus EBNA2 response element.

Table 1. Binding of purified HeLa cell CBF1 to naturally occurring and mutant promoter elements. Double-stranded oligonucleotides are derived from: EBV C-promoter (Cp); EBV C-promoter containing a double point mutation (Cp-Mut); human CD23 promoter (CD23p); heptamer site from human J Kappa gene+BamHI site (Heptamer+BamHI); heptamer site from human J Kappa gene+BamHI site containing a triple point mutation (Heptamer-BamHI). The consensus CBF1 binding site is in bold and the J kappa heptamer sequence is underlined. Binding is expressed as the % inhibition of a CBF1/C-promoter bandshift as measured with the indicated amount of competitor site. EMSA conditions were as described in (11).

| | CBF-1 Binding Site Competitor DNA | % Reduction pmol competitor | | |
|---|---|---|---|---|
| | | 0.1 | 1.0 | 10 |
| Cp | GGAAACACCCCGTGGGAAAAAATTTGGC CCTTTGTGCGGCACCCTTTTTTAAACCG (SEQ ID NO: 3) | 51 | 90 | 98 |
| Cp-Mut | GGAAACACGCCGTGGCTAAAAATTTGGG CCTTTGTGCGGCACCGATTTTTAAACCC (SEQ ID NO: 4) | 0 | 0 | 19 |
| CD23p | TCCTTCAGCCCTGTGGGAACTTGCTCCT AGGAAGTCGGGACACCCTTGAACGACGA (SEQ ID NO: 5) | 22 | 70 | 91 |
| Heptamer +BamHI | GGACTACCACTGTGGGATCCTCTGGAGG CCTGATGGTGACACCCTAGGAGACCTCC (SEQ ID NO: 6) | 0 | 31 | 75 |
| Heptamer -BamHI | GGACTACCACTGTGCCTTCCTCTGGAGG CCTGATGGTGACACGGAACGAGACCTCC (SEQ ID NO: 7) | 0 | 0 | 8 |
| Unrelated | CAAGAGACAGAGTTTCTAAGCTTATTGT- GTTCTCTGTCTCAAAGATTCGAATAACA- AATTTTAAGCATCG TTAAAATTCGTAGC (SEQ ID NO: 8) | 0 | 0 | 0 |
| ELAMp kB-1 | AAGCATCGTGGATATTCCCGGCACAGCT TTCGTAGCACCTATAAGGGCCGTGTCCA (SEQ ID NO: 9) | 0 | 8 | 44 |
| ELAMp kB-2 | TATATGCCCGGGAAAGTTTTTGTATTCC ATATACGGGCCCTTTCAAAAACATAAGG (SEQ ID NO: 10) | 2 | 27 | 51 |
| ELAM kB-3 | GATGCCATTGGGGATTTCCTCTTTACTG CTACGGTAACCCCTAAAGGAGAAATGAC (SEQ ID NO: 11) | 0 | 0 | 14 |

As shown in Table 1, the mutated binding site (Cp-mut) was approximately 250-fold weaker as a competitor than the optimal C-promoter site (Cp). An EBNA2 responsive element derived from the CD23 promoter (CD23p) was only slightly weaker (~2.5 fold) than the C-promoter site. The J kappa heptamer and adjacent BamHI site (Heptamer+ BamHI) was approximately 16-fold weaker than the C-promoter site according to this competition assay. Mutation of the GGA residues of the BamHI site to CCT (Heptamer—BamHI), which leaves the conserved heptamer sequence intact, results in an additional 40-fold reduction in its ability to compete for CBF1 binding. We therefore conclude that CBF1 does not bind the J Kappa heptamer sequence to any significant extent.

Reconstruing data on RBPJK, considerable information has already emerged regarding the structure, expression and conservation of CBF1. The amino acid sequence of CBF1 is evolutionarily conserved between species as divergent as human and Drosophila (16, 17). Studies of the tissue distribution of mouse CBF1 show that its mRNA and protein are expressed in all tissues analyzed (18). In Drosophila, the CBF1 homologue is encoded by the suppressor of hairless gene (16, 17). Thus, although CBF1 appears to be quite widely expressed during Drosophila development, it plays a key role in the specification of neuronal cell fate.

EBNA2 is known to activate a number of B-cell activation genes such as CD21 and CD23, both of which contain CBF1 sites. In the resting B-cell that EBV infects, these genes are expressed at a low level. Our results indicate CBF1 acts to tether EBNA2 to the promoters of otherwise quiescent target genes. Since EBNA2 is known to contain a transcriptional activation domain (12), the promoter bound protein could act locally to induce transcription, in a manner similar to conventional transcription factors. By utilizing CBF1 as a target for EBNA2, EBV effectively subverts the B-cells' ability to control the expression of these genes. Moreover, EBNA2 might be mimicking the cellular factor that normally binds CBF1 and activates B-cell genes in response to stimuli.

Parenthetical References

1. E. Kieff, D. Liebowitz, in Virology B. N. Fields, D. M. Knipe, Eds. (Raven Press, N.Y., 1990) pp. 1889–1920.
2. G. Miller, in Virology B. N. Fields, D. M. Knipe, Eds. (Raven Press, N.Y., 1990) pp. 1921–1958.
3. J. I. Cohen, F. Wang, J. Mack, E. Kieff, Proc. Natl. Acad. Sci. USA 86, 9558–9562 (1989).
4. W. Hammerschmidt, B. Sugden, Nature 340, 393–397 (1989).
5. M. Cordier, et al., J. Virol. 64, 1002–1013 (1990).
6. R. Fahraeus, A. Jansson, A. Ricksten, A. Sjoblom, L. Rymo, Proc. Natl. Acad. Sci. USA 87, 7390–7394 (1990).
7. X. W. Jin, S. H. Speck, J Virol. 66, 2846–2853 (1992).
8. N. S. Sung:, S. Kenney, D. Gutsch, J. S. Pagano, J. Virol. 65, 2164–2169 (1991).
9. F. Wang, H. Kikutani, S. F. Tsang, T. Kishimoto, E. Kieff, J. Virol. 65, 4101–4106 (1991).
10. U. Zimber-Strobl, et al., EMBO 12, 167–175 (1993).
11. P. D. Ling, D. R. Rawlins, S. D. Hayward, Proc. Natl. Acad. Sci. USA 90, 9237–9241 (1993).
12. P. D. Ling:, J. J. Ryon, S. D. Hayward, J. Virol. 67, 2990–3003 (1993).
13. N. Matsunami, et al., Nature 342, 934–937 (1989).
14. R. Amakawa, et al., Genomics 17, 306–315 (1993).
15. Y. Hamaguchi, N. Matsunami, Y. Yamamoto, T. Honjo, Nucleic Acids Res. 17, 9015–9026 (1989).
16. F. Schweisguth, J. W. Posakony, Cell 69, 1199–1212 (1992).
17. T. Furukawa, S. Maruyama, M. Kawaichi, T. Honjo, Cell 69, 1191–1197 (1992).
18. Y. Hamaguchi, et al., J. Biochem. 112, 314–320 (1992).
19. P. M. Lieberman, J. M. Hardwick, S. D. Hayward, J. Virol. 63, 3040–3050 (1989).
20. J. D. Dignam, R. M. Lebovitz, R. G. Roeder, Nucleic Acids Res. 11, 1475–1489 (1983).
21. S. P. Jackson, R. Tjian, Proc. Natl. Acad. Sci. USA 1989, 1781–1785 (1989).

The following examples are offered by way of illustration and not by way of limitation.

EXAMPLES

1. Protocol for CBF1—CBF1 dependent transcription factor binding assay.

A. Reagents:

CBF1: 20 µg/ml in PBS.

Blocking buffer: 5% BSA, 0.5% Tween 20 in PBS; 1 hr, RT.

Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.

$^{33}$P EBNA2 10x stock: $10^{-8}$–$10^{-6}$M "cold" EBNA2 homolog supplemented with 200,000–250,000 cpm of labeled EBNA2 homolog (Beckman counter). Place in the 4° C. microfridge during screening.

Protease inhibitor cocktail (1000X): 10 mg Trypsin Inhibitor (BMB #109894), 10 mg Aprotinin (BMB #236624), 25 mg Benzamidine (Sigma #B-6506), 25 mg Leupeptin (BMB #1017128), 10 mg APMSF (BMB #917575), and 2 mM NaVo$_3$ (Sigma # S-6508) in 10 ml of PBS.

B. Preparation of assay plates:

Coat with 120 µl of stock CBF1 per well overnight at 4° C.

Wash 2X with 200 µl PBS.

Block with 150 µl of blocking buffer.

Wash 2X with 200 µl PBS.

C. Assay:

Add 80 µl assay buffer/well.

Add 10 µl compound or extract.

Add 10 µl $^{33}$P-EBNA-2 (20,000–25,000 cpm/0.3 pmoles/well=3×$10^{-9}$M final concentration).

Shake at 25C. for 15 min.

Incubate additional 45 min. at 25C.

Stop the reaction by washing 4X with 200 µl PBS.

Add 150 µl scintillation cocktail.

Count in Topcount.

D. Controls for all assays (located on each plate):

a. 1% Non-specific binding (no CBF1 added)

b. cold EBNA2 at 80% inhibition.

2. Protocol for CBF1—CBF1 dependent transcription factor (EBNA2)—DNA binding assay.

A. Reagents:

Neutralite Avidin: 20 µg/ml in PBS.

Blocking buffer: 5% BSA, 0.5% Tween 20 in PBS; 1 hr, RT.

Assay Buffer: 100 mM KCl, 20 mM HEPES pH 7.6, 0.25 mM EDTA, 1% glycerol, 0.5% NP-40, 50 mM BME, 1 mg/ml BSA, cocktail of protease inhibitors.

$^{33}$P EBNA2 10X stock: $10^{-6}$–$10^{-8}$M "cold" EBNA2 homolog supplemented with 200,000–250,000 cpm of labeled EBNA2 homolog (Beckman counter) and $10^{-6}$–$10^{-8}$M CBF1. Place in the 4° C. microfridge during screening.

Protease inhibitor cocktail (1000X): 10 mg Trypsin Inhibitor (BMB #109894), 10 mg Aprotinin (BMB #236624), 25 mg Benzamidine (Sigma # B-6506), 25 mg Leupeptin (BMB #1017128), 10 mg APMSF (BMB #917575), and 2 mM NaVo$_3$ (Sigma # S-6508) in 10 ml of PBS.

Oligonucleotide stock: (specific biotinylated). Biotinylated oligo at 17 pmole/µl, EBNA2 site:

(BIOTIN)-GGA AAC ACG CCG TGG GGA AAA ATE TGG C anti-sense-CCT TTG TGC GGC ACC CTT TTT TAA ACC G (SEQ ID NO: 3)

B. Preparation of assay plates:

Coat with 120 µl of stock N-Avidin per well overnight at 4° C.

Wash 2X with 260 µl PBS.

Block with 150 µl of blocking buffer.

Wash 2X with 200 µl PBS.

C. Assay:

Add 40 µl assay buffer/well.

Add 10 µl compound or extract.

Add 10 µl $^{33}$P-EBNA-2 (20,000–25,000 cpm/0.1–10 pmoles/well=$10^{-9}$–$10^{-7}$M final concentration).

Shake at 25C for 15 min.

Incubate additional 45 min. at 25C.

Add 40 µl oligo mixture (1.0 pmoles/40 ul in assay buffer with 1 ng of ss-DNA)

Incubate 1 hr at RT.

Stop the reaction by washing 4X with 200 µl PBS.

Add 150 µl scintillation cocktail.

Count in Topcount.

D. Controls for all assays (located on each plate):

a. Non-specific binding (no oligo added)

b. Specific soluble oligo at 80% inhibition.

All publications mad patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A method of identifying a candidate pharmacological agent which interferes with the selective binding of C-promoter binding factor 1 (CBF1) to a transcription factor, said method comprising the steps of:

expressing a recombinant nucleic acid comprising the nucleotide sequence set forth as SEQ ID NO: 1 and purifying the resulting CBF1 protein;

forming a mixture comprising said purified CBF1 protein, said transcription factor, and a compound;

incubating said mixture under conditions whereby, but for the presence of said compound, said purified CBF1 protein selectively binds to said transcription factor; and detecting the presence or absence of the selective binding of said purified CBF1 protein to said transcription factor, wherein the absence of said selective binding indicates that said compound is a candidate pharmacological agent which interferes with the binding of said CBF1 protein to said transcription factor.

2. The method according to claim 1, wherein said transcription factor is Epstein-Barr virus Nuclear Antigen 2 (EBNA2).

3. A method of identifying a candidate pharmacological agent which interferes with the formation of a transcription complex, said method comprising the steps of:

expressing a recombinant nucleic acid comprising the nucleotide sequence set forth as SEQ ID NO: 1 and purifying the resulting CBF1 protein;

forming a mixture comprising said purified CBF1 protein, a transcription factor which selectively binds said CBF1 protein, a nucleic acid sequence comprising the nucleotide sequence GGGA, and a compound;

incubating said mixture under conditions whereby, but for the presence of said compound, said transcription complex is formed, wherein said transcription complex comprises said purified CBF1 protein and said transcription factor selectively bound, directly or indirectly, to said nucleic acid sequence; and detecting the presence or absence of said transcription complex, wherein the absence of said transcription complex indicates that said compound is a candidate pharmacological agent which interferes with the formation of said transcription complex.

4. The method according to claim 3, wherein said transcription factor is EBNA2.

5. The method according to claim 3, wherein:

said transcription factor comprises a label, said mixture further comprises a receptor immobilized on a solid substrate and said nucleic acid sequence further comprises a ligand which specifically binds to said receptor, said incubating step further comprises incubating said mixture under conditions whereby said receptor binds to said ligand, said method further comprises a step of separating from said solid substrate a fraction of said mixture, which fraction comprises said label if said transcription complex is not formed, and said detecting step comprises detecting the presence or absence of said label on said solid substrate, wherein the absence of said label on said solid substrate indicates that said compound is a candidate pharmacological agent which interferes with the formation of said transcription complex.

* * * * *